(12) United States Patent
Nassif et al.

(10) Patent No.: US 7,881,785 B2
(45) Date of Patent: Feb. 1, 2011

(54) METHOD AND APPARATUS FOR DEFROSTING A DEFIBRILLATION ELECTRODE

(75) Inventors: Rabih C. Nassif, Bothell, WA (US); Peter M. Peterson, Bothell, WA (US)

(73) Assignee: Cardiac Science Corporation, Bothell, WA (US)

( * ) Notice: Subject to any disclaimer, the term of this patent is extended or adjusted under 35 U.S.C. 154(b) by 485 days.

(21) Appl. No.: 12/055,817

(22) Filed: Mar. 26, 2008

(65) Prior Publication Data

US 2009/0248128 A1   Oct. 1, 2009

(51) Int. Cl.
*A61N 1/18* (2006.01)

(52) U.S. Cl. .................... 607/5; 607/6; 607/8
(58) Field of Classification Search .......... 607/4–8
See application file for complete search history.

(56) References Cited

U.S. PATENT DOCUMENTS

| | | | |
|---|---|---|---|
| 5,402,884 A | 4/1995 | Gilman et al. |
| 5,579,919 A | 12/1996 | Gilman et al. |
| 5,645,571 A | 7/1997 | Olson et al. |
| 5,697,955 A | 12/1997 | Stolte |
| 5,700,281 A | 12/1997 | Brewer et al. |
| 5,792,190 A | 8/1998 | Olson et al. |
| 5,797,969 A | 8/1998 | Olson et al. |
| 5,817,151 A | 10/1998 | Olson et al. |
| 5,850,920 A | 12/1998 | Gilman et al. |
| 5,897,576 A | 4/1999 | Olson et al. |
| 5,919,212 A | 7/1999 | Olson et al. |
| 5,955,956 A | 9/1999 | Stendahl et al. |
| 5,984,102 A | 11/1999 | Tay |
| 6,029,085 A | 2/2000 | Olson et al. |
| 6,148,233 A | 11/2000 | Owen et al. |
| 6,173,203 B1 | 1/2001 | Barkley et al. |
| 6,246,907 B1 | 6/2001 | Lin et al. |

(Continued)

FOREIGN PATENT DOCUMENTS

WO   WO 2006/117679   5/2006

(Continued)

OTHER PUBLICATIONS

*Gecko-Inspired Nanotube-Based Self-Cleaning Adhesives*, by Sunny Sethi et al., Nano Letters, 2008, vol. I, No. 3, 822-855. 4 Pgs.

(Continued)

*Primary Examiner*—Scott M Getzow
*Assistant Examiner*—Joseph M Dietrich
(74) *Attorney, Agent, or Firm*—Patterson Thuente Christensen Pedersen, P.A.

(57) ABSTRACT

A device and method for defrosting a defibrillation electrode are provided. This includes an automated external defibrillator that is capable of defrosting one or more frozen electrodes. The device is includes a portable housing containing a battery powered energy source and a controller as well as at least a pair of electrodes which are operably coupled to the housing. The electrodes are designed for attachment to the chest of a patient in need of resuscitation and contain a conductive interface medium that has temperature dependent properties. A controller is configured to selectively heat the conductive interface medium by applying limited electrical impulses and raise the electrode temperature to a desired temperature range.

19 Claims, 19 Drawing Sheets

U.S. PATENT DOCUMENTS

| | | |
|---|---|---|
| 6,263,238 B1 | 7/2001 | Brewer et al. |
| 6,289,243 B1 | 9/2001 | Lin et al. |
| 6,321,113 B1 | 11/2001 | Parker et al. |
| 6,658,290 B1 | 12/2003 | Lin et al. |
| 6,668,192 B1 | 12/2003 | Parker et al. |
| 6,993,386 B2 | 1/2006 | Lin et al. |
| 7,006,865 B1 | 2/2006 | Cohen et al. |
| 7,020,520 B2 | 3/2006 | Olson et al. |
| 7,065,401 B2 | 6/2006 | Worden |
| 7,132,161 B2 | 11/2006 | Knowles et al. |
| 7,452,452 B2 | 11/2008 | Ren et al. |
| 7,526,345 B2 | 4/2009 | Covey et al. |
| 2004/0240144 A1 | 12/2004 | Schott et al. |
| 2008/0169059 A1 | 7/2008 | Messersmith et al. |
| 2008/0245548 A1 | 10/2008 | Fu et al. |
| 2009/0011232 A1 | 1/2009 | Dai et al. |
| 2009/0238815 A1 | 9/2009 | Udipi et al. |

FOREIGN PATENT DOCUMENTS

| | | |
|---|---|---|
| WO | WO 2006/048847 | 11/2006 |
| WO | WO 2007/124477 | 11/2007 |
| WO | WO 2009/016546 | 2/2009 |

OTHER PUBLICATIONS

*Carbon nanotube-based synthetic gecko tapes*, by Liehui Ge et al., Department of Polymer Science, University of Akron, Akron, Ohio 44325-3909; and Department of Materials Science and Engineering, Rensselaer Polytechnic Institute, Troy, NY 12180-3590, 10792-10795, PNAS, Jun. 26, 2007, vol. 104, No. 26. 4 Pgs.

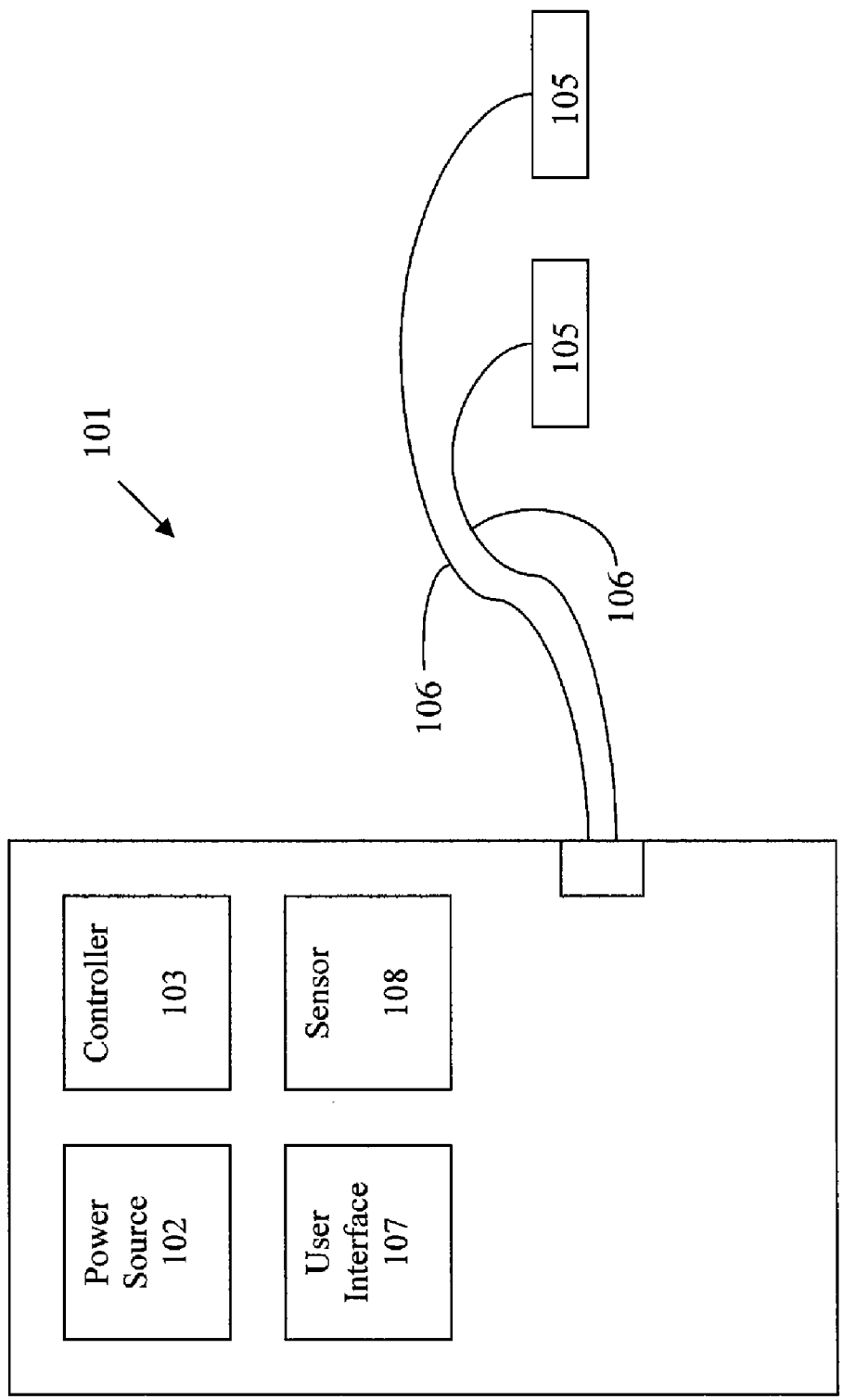

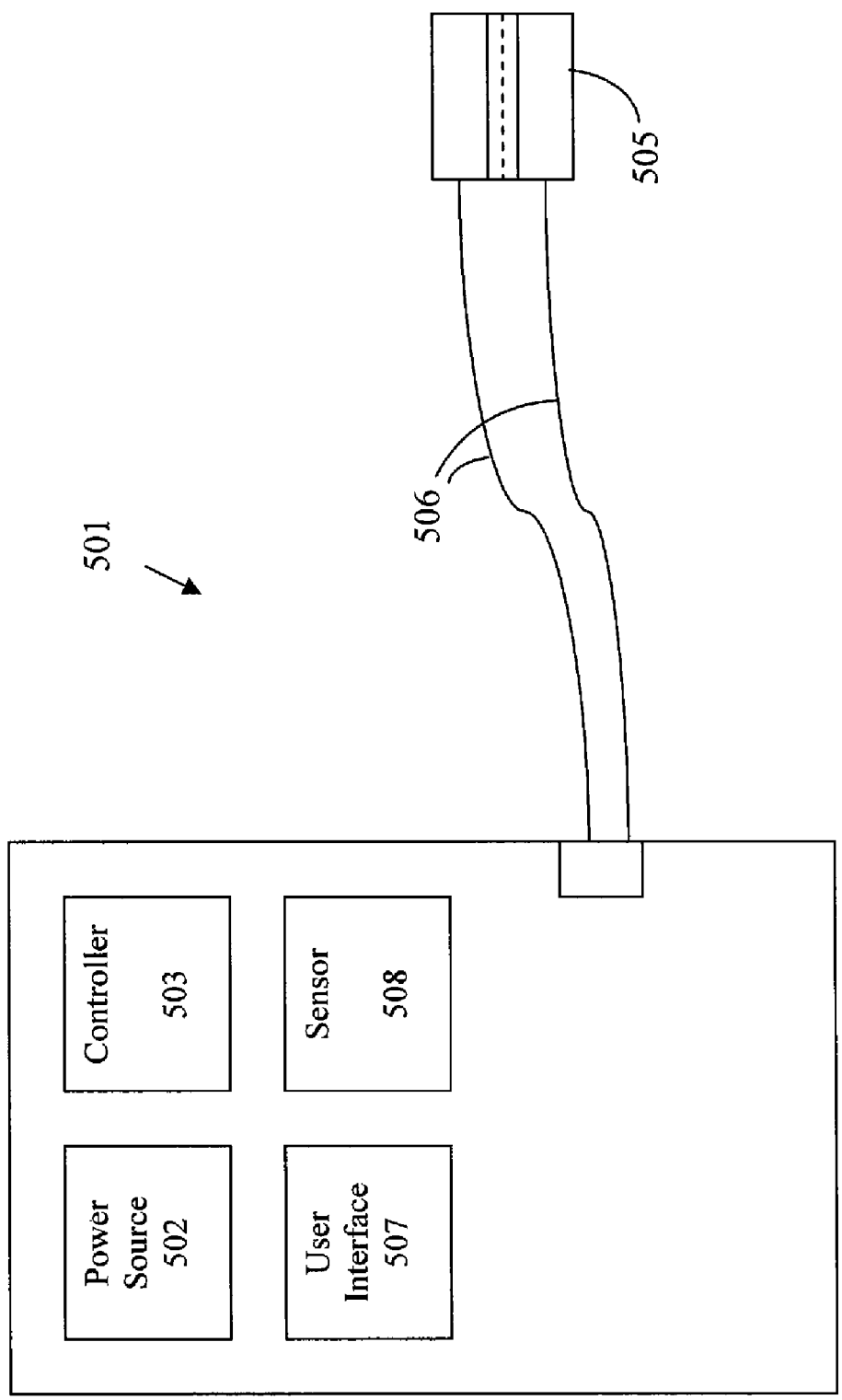

METHOD AND APPARATUS FOR DEFROSTING A DEFIBRILLATION ELECTRODE

TECHNICAL FIELD

The present invention relates to methods and devices for resuscitating a patient. More particularly, the present invention relates to electric defibrillators and thawing frozen defibrillation electrodes used with electric defibrillators.

BACKGROUND OF THE INVENTION

Many techniques exist for resuscitating a patient suffering from a life threatening condition. Patient conditions that may require resuscitation include, but are not limited to, cardiac arrest, bradycardia, tachycardia, ventricular fibrillation and respiratory arrest. One example of a technique for resuscitating a patient is to use an electric defibrillator to apply electrical energy to the patient.

The human heart contracts when stimulated by an intrinsic electric impulse generated by the human body itself. When a patient undergoes some form of cardiac arrest, or where the heart has stopped beating or is beating at an unsafe rate, it is often valuable to apply an unnatural electrical impulse to restart or sync a human heart so that it can continue to function and thus keep a patient alive. Electrical impulse therapy is often administered using an electric defibrillator. An electric defibrillator typically includes a power source and at least two defibrillation electrodes that provide a connection with the skin of a patient for electricity to be administered to the patient. Typically, defibrillation electrodes are disposed upon the chest region of a patient such that electrical energy can be administered to the patient.

Portable versions of electric defibrillators have existed since the 1960's. The use of these devices is now widespread. Both emergency and non-emergency personnel often have access to portable versions of electric defibrillators, known as automated external defibrillators (AEDs), in case of emergencies. Examples of such AEDs include: Cardiac Science's Powerheart®, Medtronic's LIFEPAK®, Defibtech's Lifeline™, Phillips' HeartStart™, and Zoll's AED Plus®.

It is important that these AEDs be continuously operational and ready for use on a moment's notice. Any delay in the ability of a rescuer to use such a device in an emergency can mean the difference between life and death for a patient. One such delay may occur as a result of the defibrillation electrodes being frozen. Because AEDs are highly portable, they are often stored in automobiles or other unheated places. In cold weather, portions of the defibrillation electrodes may freeze. In order for a defibrillation electrode to properly deliver an appropriate electrical impulse as described, the electrode must not be frozen. In current practice, if an electrode is frozen, a rescuer must either replace the electrode with an unfrozen one, or use external means such as a heater to thaw the electrode. Often, in critical situations, a frozen electrode results in valuable time wasted and in the worst case may result in death to a patient.

SUMMARY OF THE INVENTION

Accordingly, the present invention overcomes the problems of the prior art by providing a method and device to efficiently defrost defibrillation electrodes. In one embodiment, an automated external defibrillator with defrosting capabilities includes a portable housing containing a battery powered energy source and a controller. The embodiment also includes at least a pair of electrodes operably coupled to the housing. In this embodiment, the electrodes are releasably attachable to an external portion of a patient in need of resuscitation. Further, each of the electrodes includes a conductive interface medium having physical properties dependent upon a desired temperature range of about 32° F. to 122° F. Also, the controller is configured to selectively heat the conductive interface medium by applying a limited amount of electrical impulse from the energy source to raise the temperature of the conductive interface medium toward the desired range.

According to another embodiment of the present invention, an automated external defibrillator with defrosting capabilities includes a pair of preconnected electrodes including an outer hydrogel layer on each electrode having physical properties dependent upon a normal temperature range of about 32° F. to 122° F. Also included is a housing having a battery powered energy source and a controller that selectively heats the hydrogel layer by applying a limited amount of electrical impulse to raise the temperature of the hydrogel layer to the normal range.

In yet another embodiment according to the present invention, a method of controlling the operating conditions of defibrillation electrodes of an automated external defibrillator includes providing a pair of electrodes releasably attachable with an external portion of a patient in need of resuscitation where each electrode has a conductive interface medium having physical properties dependent upon a desired temperature range of about 32° F. to 122° F. The method also including automatically causing the automated external defibrillator to deliver a limited electrical impulse to the defibrillation electrodes so as to heat the defibrillation electrodes to the desired temperature range.

BRIEF DESCRIPTION OF THE DRAWINGS

The invention may be more completely understood in consideration of the following detailed description of various embodiments of the invention in connection with the accompanying drawings, in which:

FIG. 1 illustrates generally an example of an electric defibrillator.

FIG. 5 illustrates generally an electric defibrillator according to the subject matter disclosed herein.

DETAILED DESCRIPTION OF THE PREFERRED EMBODIMENTS

Figure 2A:
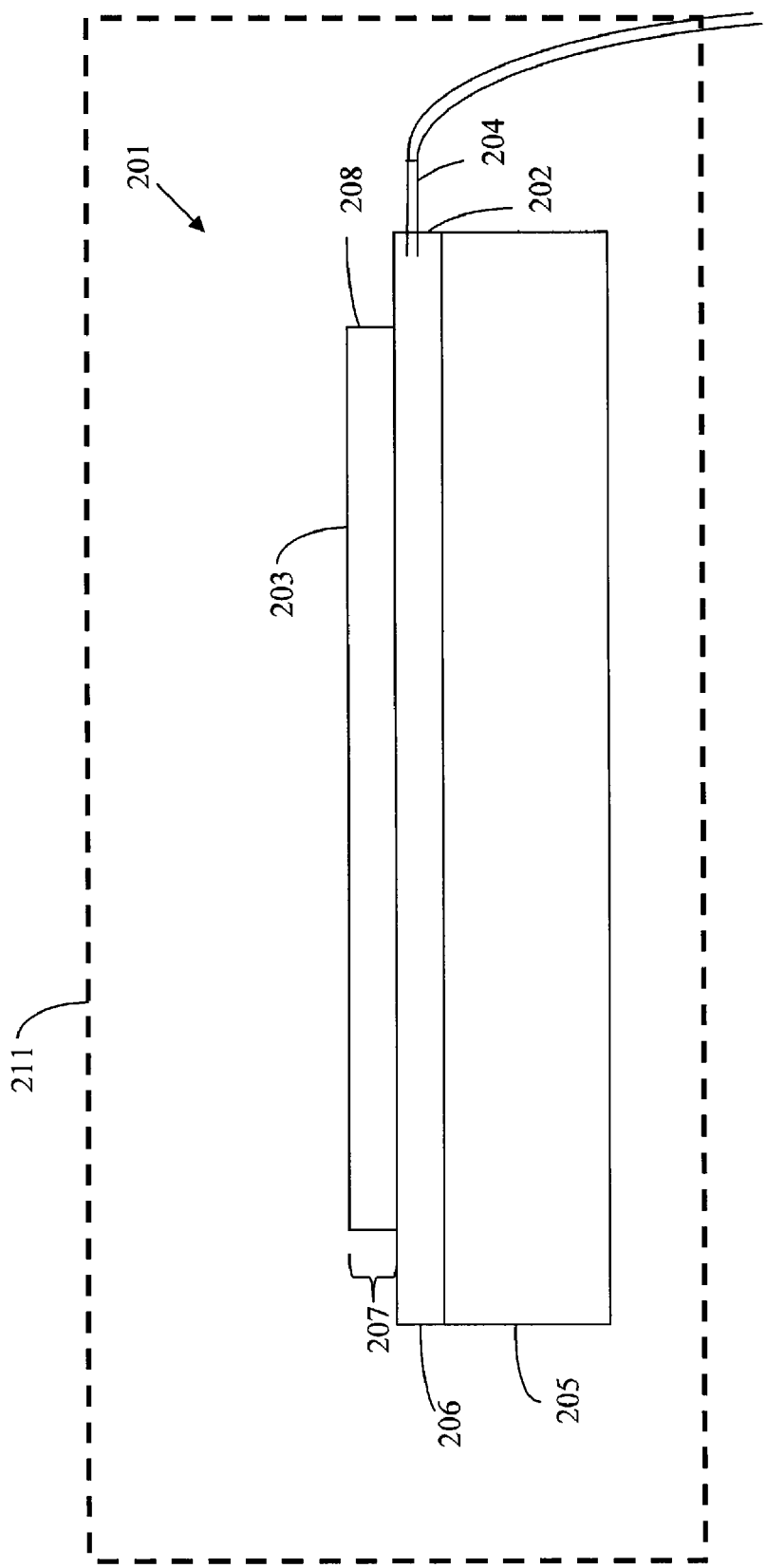
FIG. 2a illustrates generally an example of a defibrillator electrode.

The invention may be embodied in other specific forms without departing from the essential attributes thereof, therefore, the illustrated embodiments should be considered in all respects as illustrative and not restrictive.

FIG. 1 illustrates generally an example of an electric defibrillator 101. In various embodiments, electric defibrillator 101 includes one or more power sources 102. In various embodiments, power source 102 includes one or more batteries. In various embodiments, power source 102 also includes one or more capacitors. In various embodiments, power source 102 is adapted to provide energy sufficient to provide an electrical impulse capable of stimulating a heart. In various embodiments, defibrillator 101 includes controller 103. Controller 103 is adapted to initiate, adjust, and/or monitor functions of defibrillator 101. In various embodiments, controller 103 is adapted to initiate or adjust delivery of an electric impulse for purposes of providing electrical therapy to a patient. In some embodiments, defibrillator 101 further includes user interface 107. User interface 107 is adapted to allow communication between a user and controller 103. In various embodiments, user interface 107 is adapted to allow a user to program controller 103.

In various embodiments, defibrillator 101 also includes at least one electrode 105. In various embodiments, electrode 105 is connected to electrical conductor 106 such that electrode 105 is in electrical connection with power source 102. In various embodiments, electrode 105 is adapted to be placed in contact with a patient and serve as a connection for delivery of electrical energy to a patient. Typically, at least two electrodes 105 are required so that an electrical connection is provided across the body of a patient such that a current may be driven through the body of a patient to stimulate the patient's heart.

In various embodiments, defibrillator 101 further includes at least one sensor 108. These sensors 108 are generally operably connected to controller 103. Sensor 108 may be adapted to determine conditions of components of defibrillator 101. In one embodiment, sensor 108 is adapted to determine a temperature of electrode 105. In one embodiment, sensor 108 is adapted to determine the amount of energy stored in power source 102. In various embodiments, sensor 108 is adapted to determine conditions of components of defibrillator 101. In one embodiment, sensor 108 is adapted to determine whether electrode 105 is frozen. In various embodiments, sensor 108 is adapted to determine conditions external to defibrillator 101. In some embodiments, sensor 108 may also be capable of detecting defibrillator movement or other events commonly occurring prior to defibrillation, such as movement of a defibrillator panel.

Generally, electrode 105 is a defibrillation electrode adapted to apply an electric impulse to a patient. If electrode 105 is frozen, or very cold, it will likely not function properly to apply an electrical impulse to a patient. Therefore, a frozen electrode 105 must be defrosted quickly and efficiently so that electrode 105 will function effectively to apply an electrical impulse to a patient. More specifically, certain components of the electrode such as a hydrogel layer or other conductive interface medium can readily freeze when temperatures drop below a desired temperature range. The physical properties of the conductive interface medium often requires a desired, normal temperature range for operation to generally be about 32° F. to 122° F. Such a range is needed for safe and reliable defibrillation operation. Consequently, the controller of the present invention is designed to selectively heat the conductive interface medium by applying a limited amount of electrical impulse from the energy source to raise the temperature of the conductive interface medium to the desired range.

In embodiments of the present invention, using the controller to selectively signal the electrical impulses or other means to warm and defrost the electrodes can be done in a variety of ways. As mentioned, a sensor 108 in the defibrillator may detect a freezing temperature in the proximity of the electrodes. Alternatively, a sensor that detects when the defibrillator is moved or opened can signal defrosting, as such actions will often occur just prior to defibrillation. Sending sensor data to the controller in this way will also ensure the defibrillator is ready for use at desired times. Additional signaling events may follow routine or automatic self testing operations by the defibrillator.

The controller may be programmed with various safety features to recognize and prevent continuous or repetitive signaling data that might result in significant battery usage and drain. Such features ensure that the defibrillator will be sufficiently charged for proper use.

FIG. 2a illustrates generally one example of a defibrillation electrode 201. Defibrillation electrode 201 includes a lead location 202 and a patient contact surface 203. In various embodiments, patient surface 203 is adapted to be placed in contact with a patient in order to deliver electrical therapy to the patient. Lead location 202 is adapted to connect an electrode 201 to an electrical conductor 106. In an embodiment, lead location 202 includes a lead 204 which may be made of a conductive material. Electrode 201 further includes base layer 205. In various embodiments, base layer 205 is any non-conductive material. According to the embodiment illustrated in FIG. 2a, lead 204 extends out from electrode 201 in order to create an electrical connection with power source 102. Electrode 201 further includes conductive layer 206. In various embodiments, layer 206 may be made of foil or other conductive material. In various embodiments, conductive layer 206 is disposed in contact with lead 204 to provide electrical connectivity between lead 204 and conductive layer 206.

Electrode 201 further includes patient contact portion 207. Conductive layer 206 is adapted to transfer voltage or current from lead 204 to patient contact portion 207. In some embodiments, patient contact portion 207 may be entirely comprised of a hydrogel layer or conductive interface medium 208 disposed in electrical contact with conductive layer 206. The conductive interface medium 208 is generally comprised of a conductive gel or similar material. However, in some cases the conductive interface medium 208 may be comprised of a tape or an adhesive of various kinds. For example, use of a nanopillar tape comprised of sheets of elastic, sticky polymers of a multiplicity of nanopillars or related medical tapes might be used in some designs. In general, hydrogel layer 208 is adapted to reduce variations in conductance when patient contact surface 203 is placed in contact with a patient and electrical energy is applied to electrode 201. The hydrogel 208 may have both conductive properties for transmitting energy and adhesive properties for attaching to a patient's skin. Specifically, the hydrogel helps make the electrodes releasably attachable to an external portion of a patient in need of resuscitation.

Figure 2B:
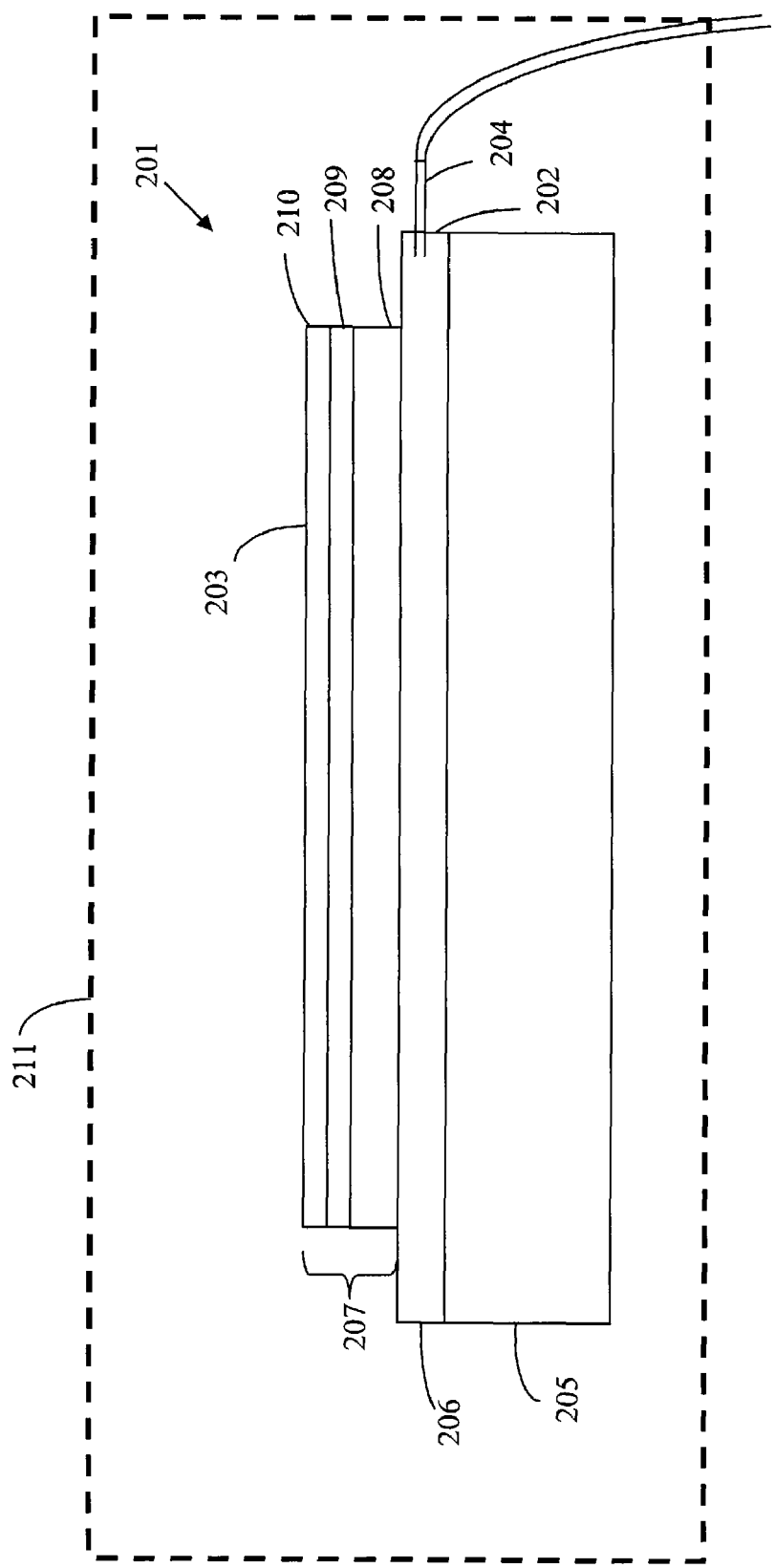
FIG. 2b illustrates generally an alternate example of a defibrillator electrode.

Patient contact portion 207 may alternatively be comprised of a number of layers as set forth in FIG. 2b. One layer being a hydrogel layer 208 disposed in electric contact with conductive layer 206. Patient contact portion 207 may further include a foil layer 209 in contact with hydrogel layer 208. In various embodiments foil layer 209 is a thin layer of conductive material adapted to transfer energy through hydrogel layer 208 to the patient contact surface 203. Patient contact portion 207 may further include an adhesive layer 210. Adhesive layer 210 is adapted to secure patient contact surface 203 to the skin of a patient. In various embodiments, adhesive layer 210 is made of any material with adhesive properties that further allows conduction of electricity to the skin of a patient.

It is to be understood when reading this application that the term "frozen" as used herein includes any temperature driven malfunction of defibrillation electrode 201. In one example, electrode 201 does not function correctly because patient contact portion 207 is frozen, and therefore cannot ensure desired delivery of electrical energy to patient contact portion 207.

In various embodiments, electrode 201 is enclosed in a package 211 prior to use. Package 211 is adapted to protect the electrode prior to use to revive a patient. In one embodiment, a single electrode 201 is enclosed in package 211. In another embodiment, two or more electrodes 201 are enclosed in package 211. In various embodiments, package 211 is made of a material capable of protecting electrode 201 prior to use. In one embodiment, package 211 is a thin, flexible material. In another embodiment, package 211 is a tensile material. In various embodiments, package 211 may include additional features such as additional electrical connections.

Figure 3A:
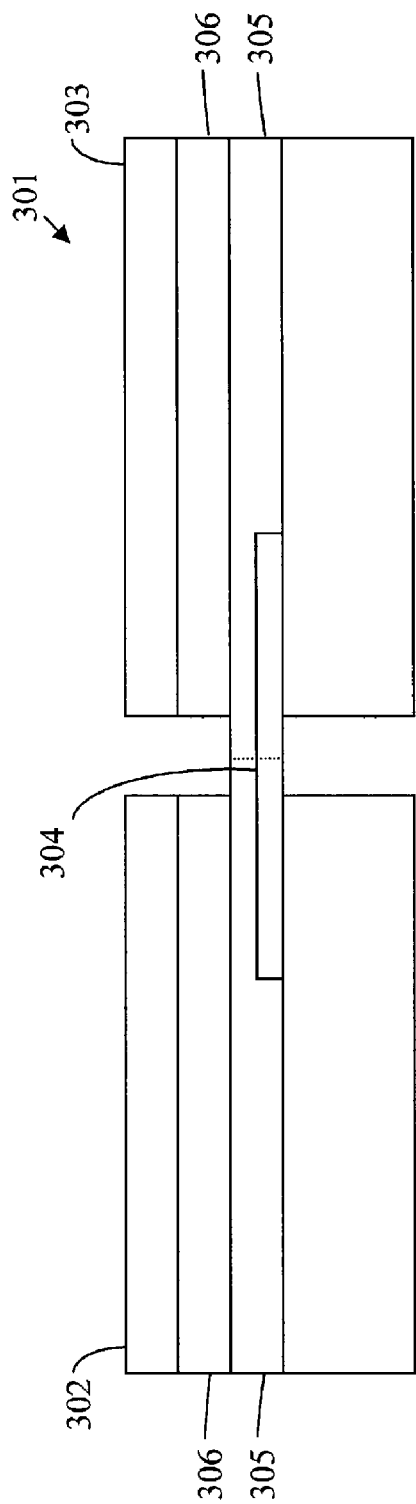
FIG. 3a illustrates generally an example of pre-connected electrodes.
Figure 3B:
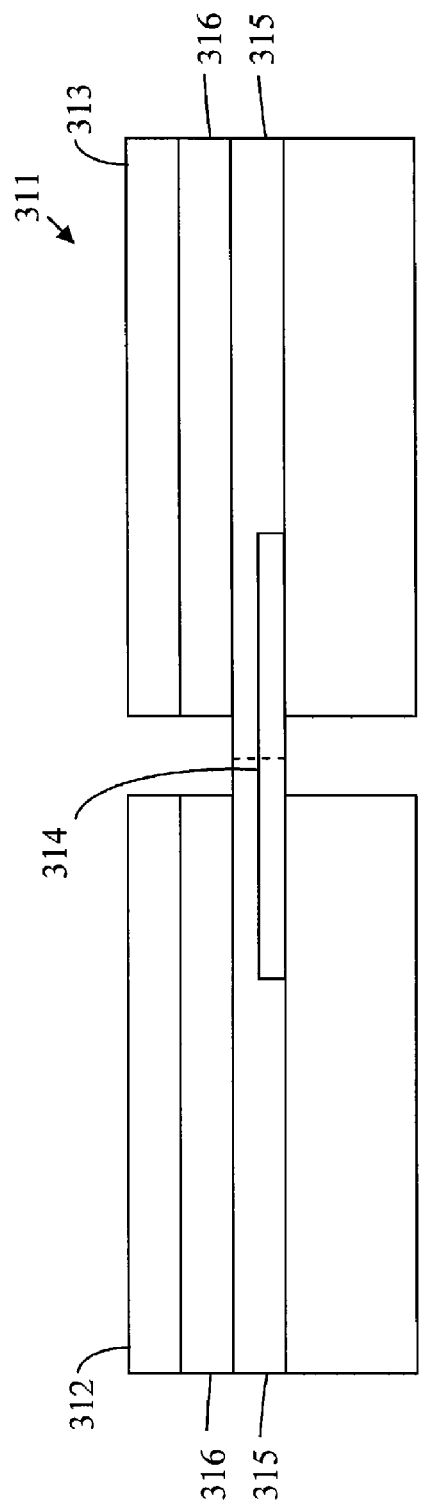
FIG. 3b illustrates generally an example of pre-connected electrodes.

FIG. 3a and FIG. 3b illustrate generally examples of pre-connected electrodes 301 and 311 respectively, in a horizontal pre-connection arrangement. Electrodes 301 and 311 are typically pre-connected so that one or more conditions of electrodes 301 and 311 can be determined by applying a current through the electrodes. According to the example of FIG. 3a, electrodes 302 and 303 are pre-connected by breakable electrode connector 304. In various embodiments, breakable electrode connector 304 is a conductive material such as a metal that is adapted to provide an electrical connection to allow current to flow between electrodes 302 and 303. In various embodiments, breakable electrode connector 304 is adapted to establish an electrical connection between hydrogel layers 305 or foil 306 of electrodes 302 and 303. Electrodes 302 and 303 are connected for test purposes prior to the use of electrodes 302 and 303 to revive a patient. To use electrodes 302 and 303 to revive a patient, breakable electrode connector 304 is broken, and an electrical connection no longer exists between electrodes 302 and 303. Although FIG. 3a only shows breakable electrical connector 304 connecting hydro-gel layers, it is to be understood that electrical connector 304 can be adapted to connect any or all layers of electrodes 302 and 303.

According to the embodiment shown in FIG. 3b, electrodes 312 and 313 are pre-connected in a horizontal orientation by perforated electrode connector 314. In various embodiments, perforated electrode connector 314 is an extension of hydrogel layer 315 that is perforated such that a rescuer can easily separate electrode 312 from electrode 313. In various embodiments, perforated electrode connector 314 is adapted to establish an electrical connection between hydrogel layers 315 of electrodes 312 and 313. Electrodes 312 and 313 are connected for test purposes prior to the use of electrodes 312 and 313 to revive a patient. To revive a patient, perforated electrode connector 314 is separated, and an electrical connection no longer exists between electrodes 312 and 313. Although FIG. 3b only shows perforated electrical connector 314 connecting hydrogel layers, it is to be understood that perforated electrical connector 314 can be adapted to connect any or all layers of electrodes 312 and 313. For example, foil layers 316 of electrodes 312 and 313 could be connected by foil shaped in a serpentine pattern as shown in FIG. 6b to provide a resistive heating element.

Figure 3C:
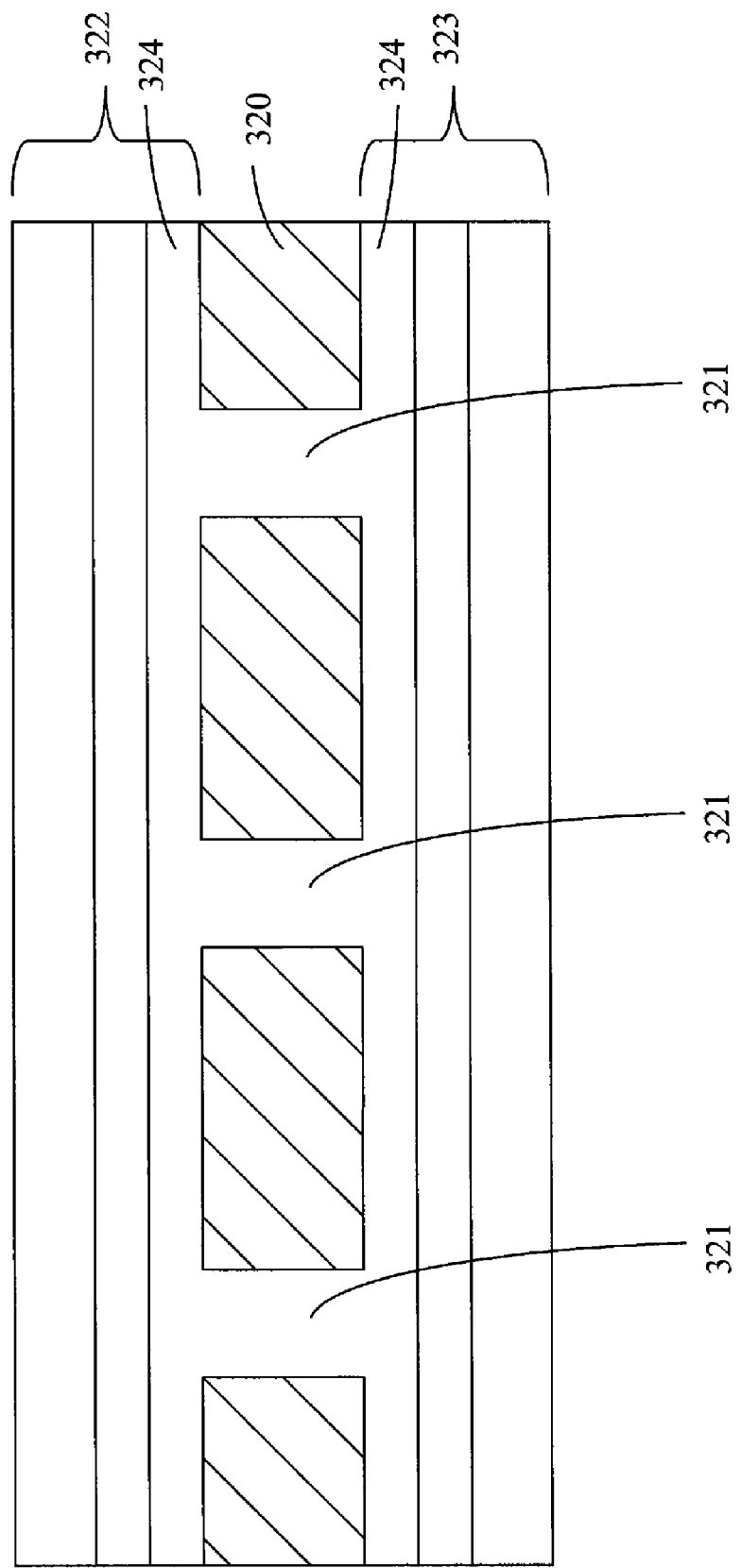
FIG. 3c illustrates generally an example of pre-connected electrodes.

FIG. 3c illustrates generally electrodes 322 and 323 pre-connected in a horizontal orientation. According to the embodiment shown in FIG. 3c, adhesive layers 324 of electrodes 322 and 323 are separated by electrode separator 320. In various embodiments, electrode separator 320 is made of a non-conductive material, and contacts both adhesive layers 324. Adhesive layers 324 typically comprising hydrogel or a similar substance. Holes 321 in electrode separator 320 allow adhesive from adhesive layers 324 to establish an electrical connection between electrode 322 and electrode 323. To revive a patient, electrode 322 and electrode 323 are removed from electrode separator 320, and electrical connection no longer exists between electrodes 322 and 323.

Figure 3D:
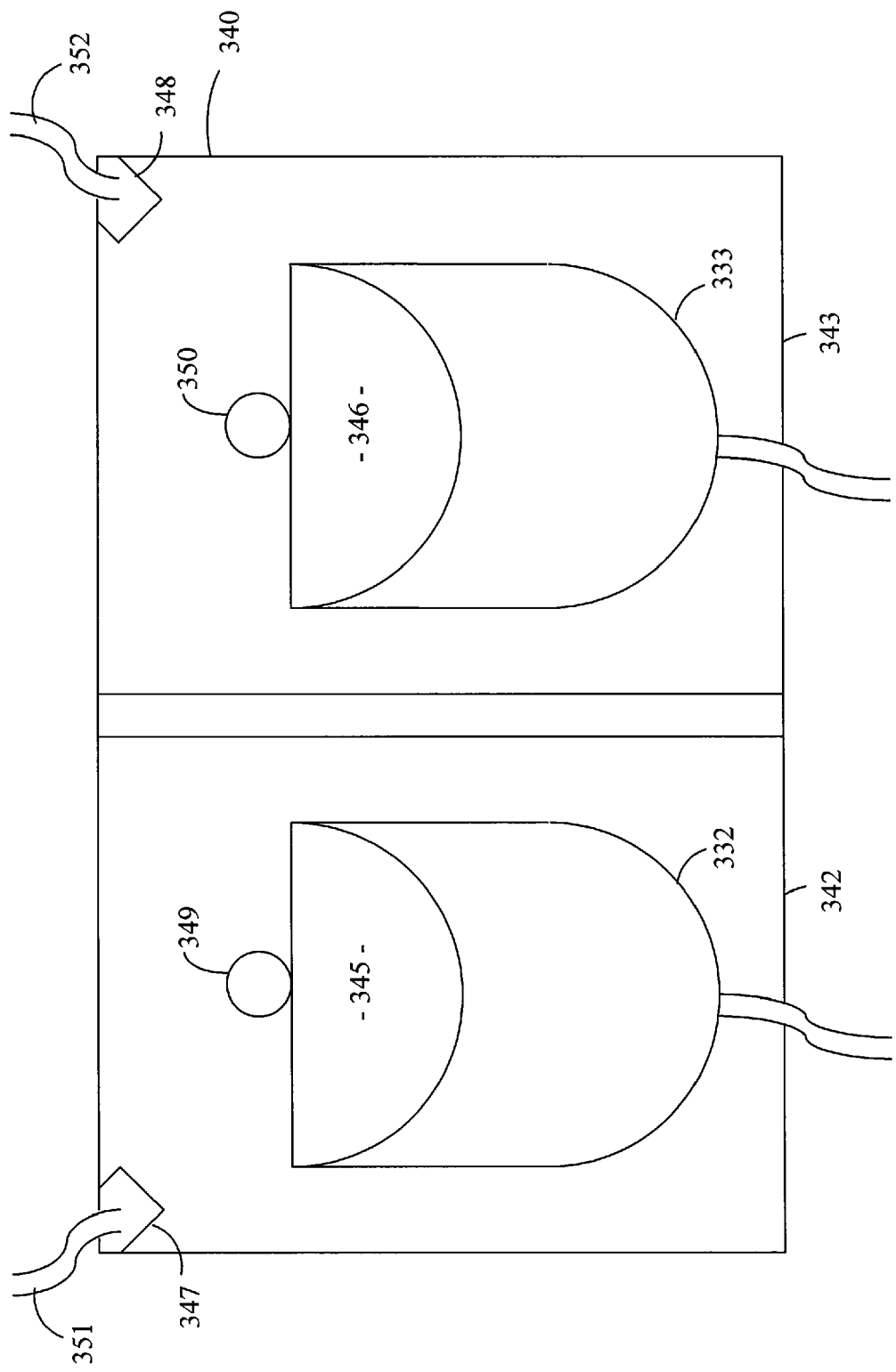
FIG. 3d illustrates generally an example of pre-connected electrodes.

FIG. 3d illustrates generally electrodes 332 and 333 pre-connected in a vertical orientation and enclosed in package 340. According to the embodiment disclosed in FIG. 3d, package 340 is a hard, tensile material. Package 340 includes two opposed interior surfaces 342 and 343. Electrode 332 is generally disposed upon interior surface 342 and electrode 333 is disposed upon interior surface 343. Prior to use, an adhesive layer 345 is located between interior surface 342 and electrode 332. Also, adhesive layer 346 is located between interior surface 343 and electrode 333. The embodiment shown in FIG. 3d shows electrodes 332 and 333 partially folded back for illustration purposes so that the components underneath the electrodes may be better understood. This configuration reveals the bottom surface of the electrodes containing adhesive layers 345 and 346 and interior electrical contacts 349 and 350. However, in most cases it is to be understood that prior to use adhesive layers 345 and 346 are fully disposed upon interior surfaces 342 and 343 without such folding.

The embodiment illustrated in FIG. 3d further includes external electrical contacts 347 and 348 and interior electrical contacts 349 and 350. Internal electrical contacts 349 and 350 are disposed on interior surfaces 342 and 343 such that interior electrical contacts 349 and 350 provide an electrical connection with adhesive surfaces 345 and 346 when adhesive layers 345 and 346 are disposed upon interior surfaces 342 and 343. Interior electrical contacts 349 and 350 are in electrical contact with external electrical contacts 347 and 348. External electrical contacts are adapted to accept an electrical connection with electrical conductors 351 and 352 such that a closed loop connection is formed with a power source connected to electrical conductors 351 and 352 and a current can be forced through electrodes 332 and 333. To revive a patient, electrode 332 and electrode 333 are removed from interior surfaces 342 and 343 and placed on a patient's chest so that interior electrical contacts 349 and 350 are no longer in electrical contact with adhesive layers 345 and 346 and electrical connection no longer exists between electrodes 332 and 333.

Figure 3E:
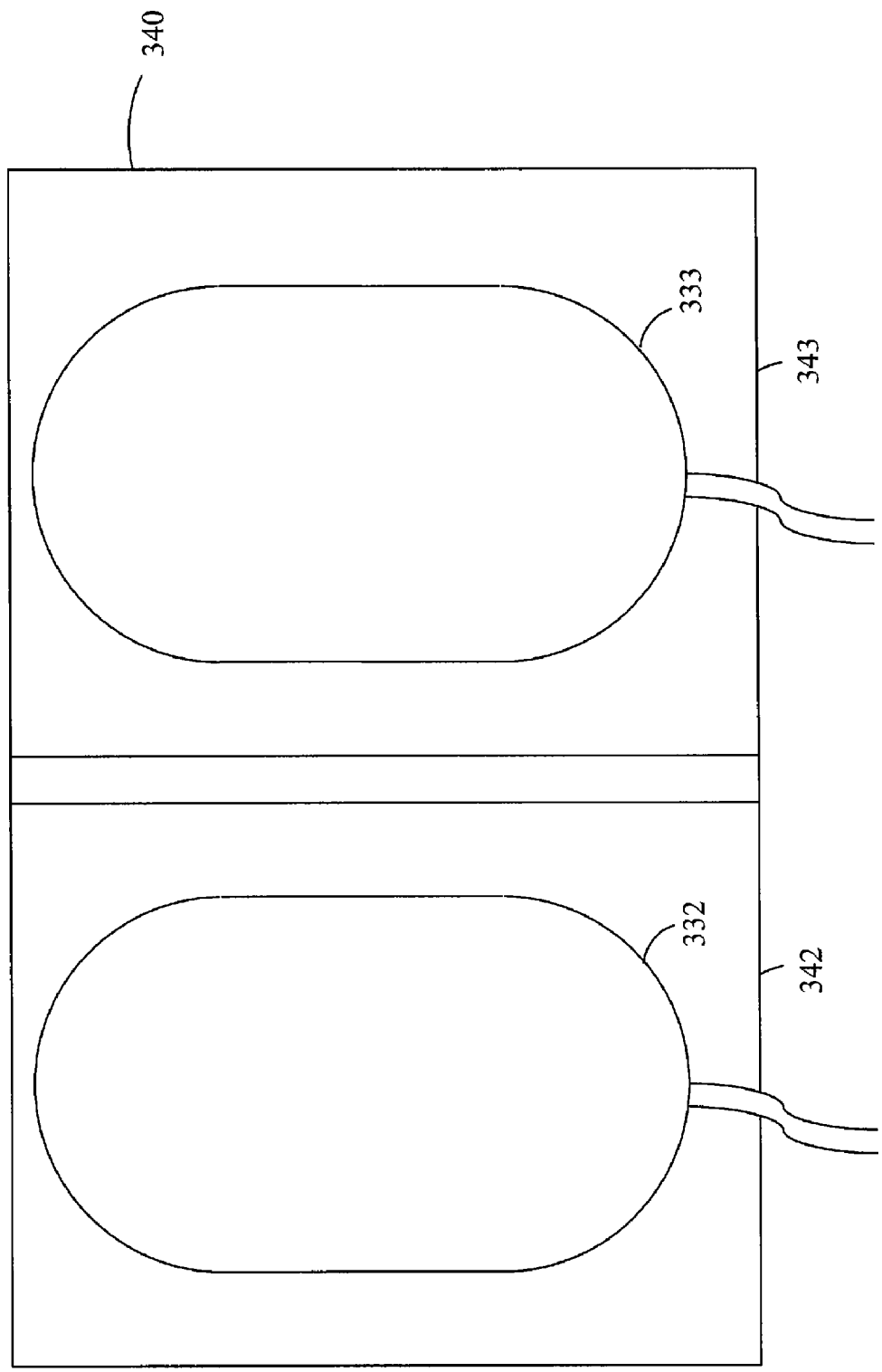
FIG. 3e illustrates generally an example of pre-connected electrodes.

FIG. 3e discloses an embodiment where electrodes 332 and 333 are disposed on interior surfaces 342 and 343. Surfaces 342 and 343 are comprised of a conductive surface such that current may travel between electrodes 332 and 333. Therefore, a connection is provided with the power source such that current can be forced through electrodes 332 and 333 via their electrical connection. The electrodes 322 and 333 are removed from surfaces 342 and 343 when used for defibrillation.

Figure 4:
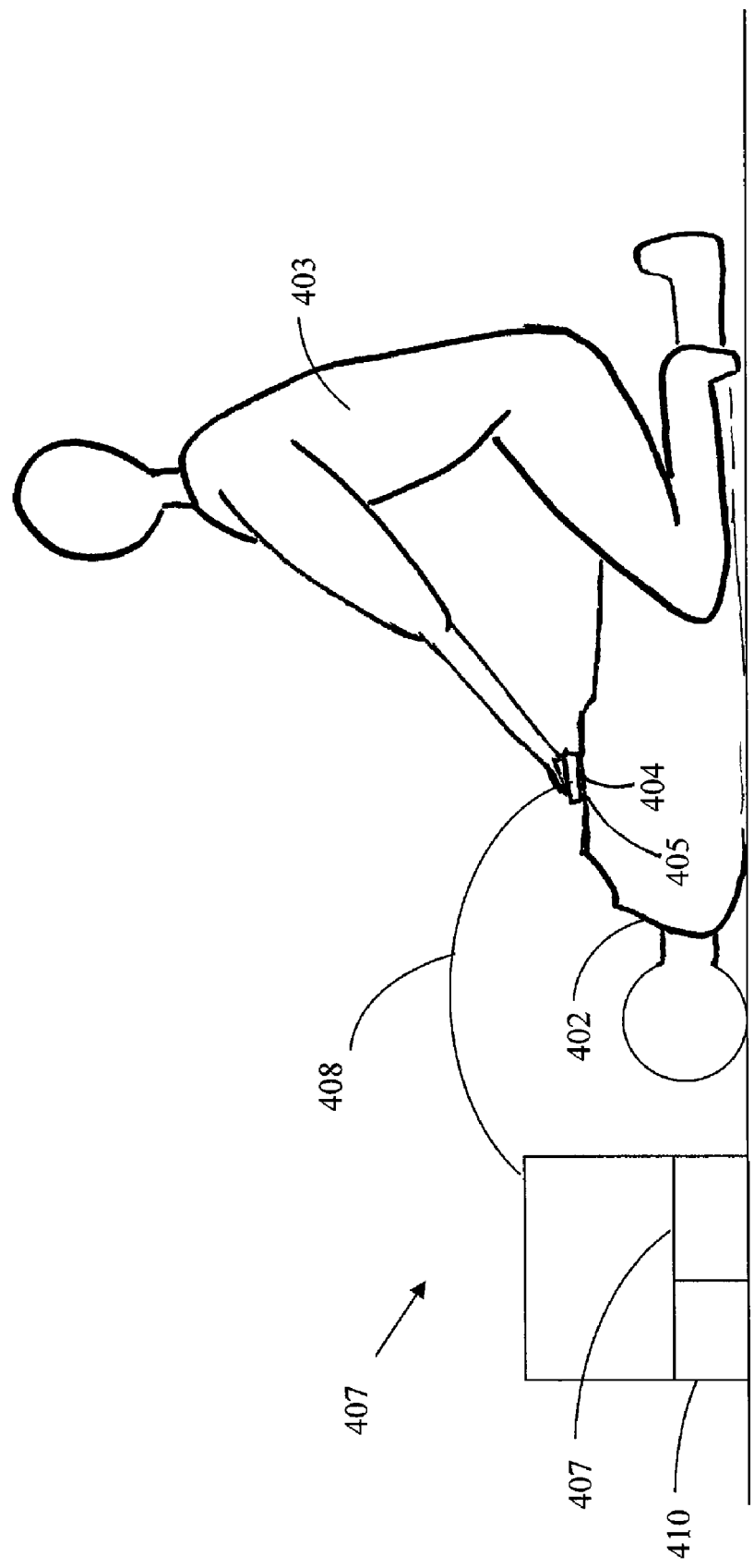
FIG. 4 illustrates generally a rescuer using an electric defibrillator on a patient.

FIG. 4 illustrates generally the use of electric defibrillator 401 to resuscitate patient 402. In the example of FIG. 4, patient 402 is in need of therapy from electric defibrillator 401. Rescuer 403 places both electrodes 404 in contact with skin 405 of patient 402. Adhesive layers of electrodes are disposed upon skin such that adhesive layers provide an electrical connection with skin 405. Electrodes 404 are electrically connected to the remainder of defibrillator 401 through electrical conductors 408. According to the example of FIG. 4, when rescuer 403 has placed electrodes 404 in contact with patient 402, rescuer 403 activates electric defibrillator 401 and an electrical impulse is applied from power source 407 through the electrodes 404 to patient 402. Controller 410 controls delivery of the electrical impulse.

FIG. 5 illustrates generally one embodiment of electric defibrillator 501 according to the subject matter disclosed herein. The example of FIG. 5 is identical to the example shown in FIG. 1, except defibrillation electrodes are pre-connected as shown in FIG. 3a, FIG. 3b, FIG. 3c, FIG. 3d, or FIG. 3e. According to the embodiment shown in FIG. 5, the connection between the pre-connected electrodes provides a current path such that a current can be driven through the electrodes. Specifically, the hydrogel layers 208 of each electrode are in electrical contact with each other. It is to be understood that any pre-connection current path that is provided between hydrogel layers 208 is within the scope of the subject matter disclosed herein.

In various embodiments, defibrillator 501 drives current through electrical conductors 506 and through hydrogel portions 208 of electrodes 505. In various embodiments, controller 503 initiates, adjusts, and/or monitors the current driven through hydrogel portions 208 of electrodes 505. In various embodiments, the current may be a DC current, an AC current, an intermittent DC current, or an intermittent AC current. In various embodiments, current is driven at a rate and intensity such that hydrogel layers 208 of electrodes 505 absorb the current and thaw electrode 505 without overheating and therefore damaging any component of electrodes 505. Controller 503 initiates, adjusts, and/or monitors driving of current into electrodes 505. The embodiments disclosed in FIG. 5 allow the ability to automatically thaw electrodes 505 and can be implemented via a programming change of controller 503.

In many cases, existing defibrillation circuits and controllers which utilize pre-connected electrodes may be used to deliver these energy bursts of electrical current directly into the electrodes. In such cases, it may be possible to achieve defrosting in even existing defibrillators by simply a programming change to the existing controller. Use of a software upgrade is particularly advantageous due to the low cost of implementation resulting from the continued use of an existing energy source and controller. Additionally, software upgrades lend themselves to an inherent ease of in-field implementation. The use of software upgrades may apply to various portable defibrillators with automated temperature sensing features as well.

Figure 6A:
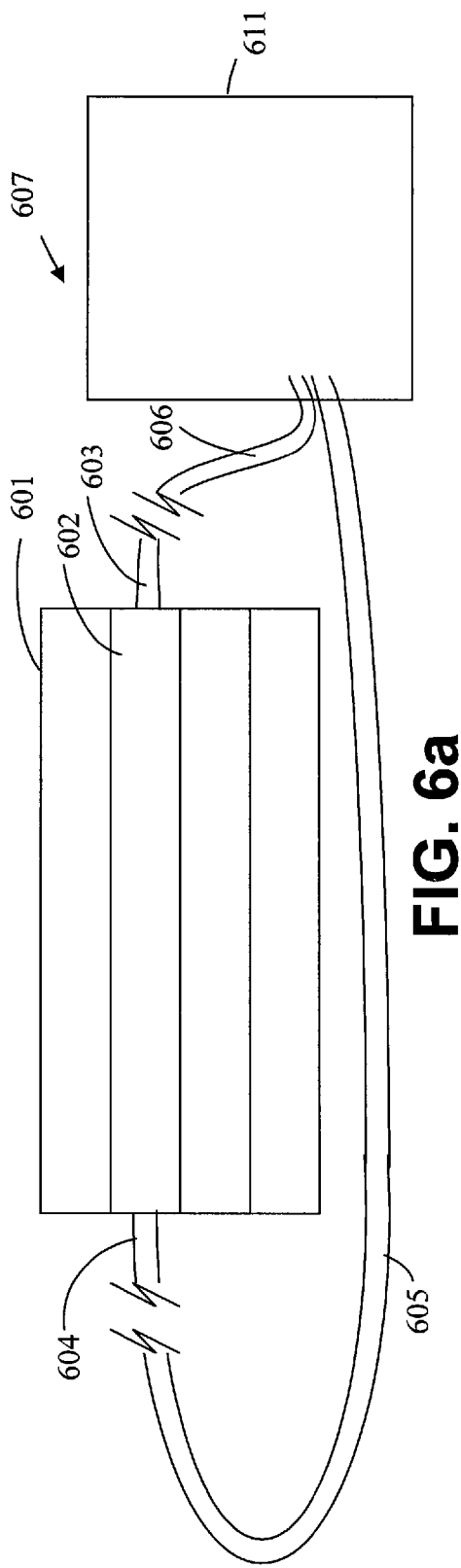
FIG. 6a and FIG. 6b illustrate generally an electric defibrillator according to the subject matter disclosed herein.
Figure 6B:
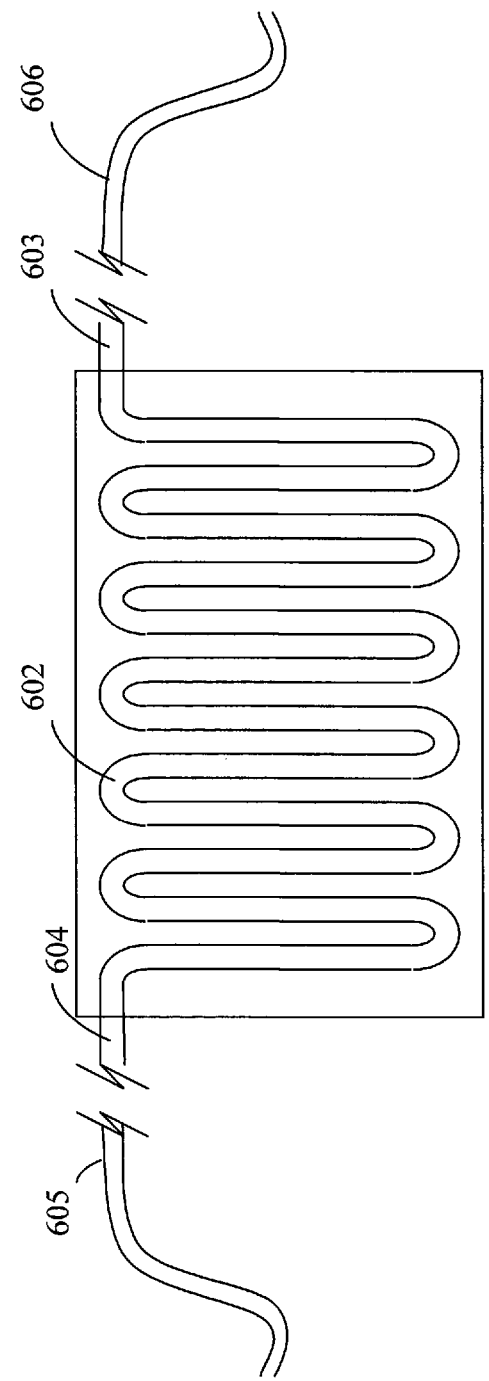

FIG. 6a and FIG. 6b illustrate generally one embodiment of defibrillator 607 adapted to thaw electrode 601 according to the subject matter disclosed herein. According to this embodiment, foil 602 of electrode 601 is used as a heating element to defrost electrode 601. FIG. 6a illustrates electrode 601. Electrode 601 is similar to electrodes 201 illustrated in FIGS. 2a and 2b, however electrode 601 includes two leads 603 and 604. In various embodiments, leads 603 and 604 are connected to electrical conductors 605 and 606 and provide an electrical connection between foil 602 and the other components located in the base 611 of the defibrillator including the power source. To heat the electrode, defibrillator 607 is adapted to direct current through foil 602. Because foil 602 is made of a conductive element, current directed through foil 602 causes heating of foil 602 and thus dissipates heat to thaw electrode 601.

In various embodiments, foil 602 is not a flat, uniform layer such as the conductive layer 206 or foil 209 illustrated in FIG. 2. FIG. 6b illustrates an alternative embodiment of foil 602 as a serpentine structure. The arrangement of foil 602 as a serpentine structure as opposed to a flat, uniform layer maximizes the ability of foil 602 to dissipate heat. In an alternative embodiment, foil 602 is arranged as a helical structure to maximize the ability of foil 602 to dissipate heat. It is to be understood that any shape, size, or structure of foil 602 is within the scope of the subject matter described herein.

Figure 7:
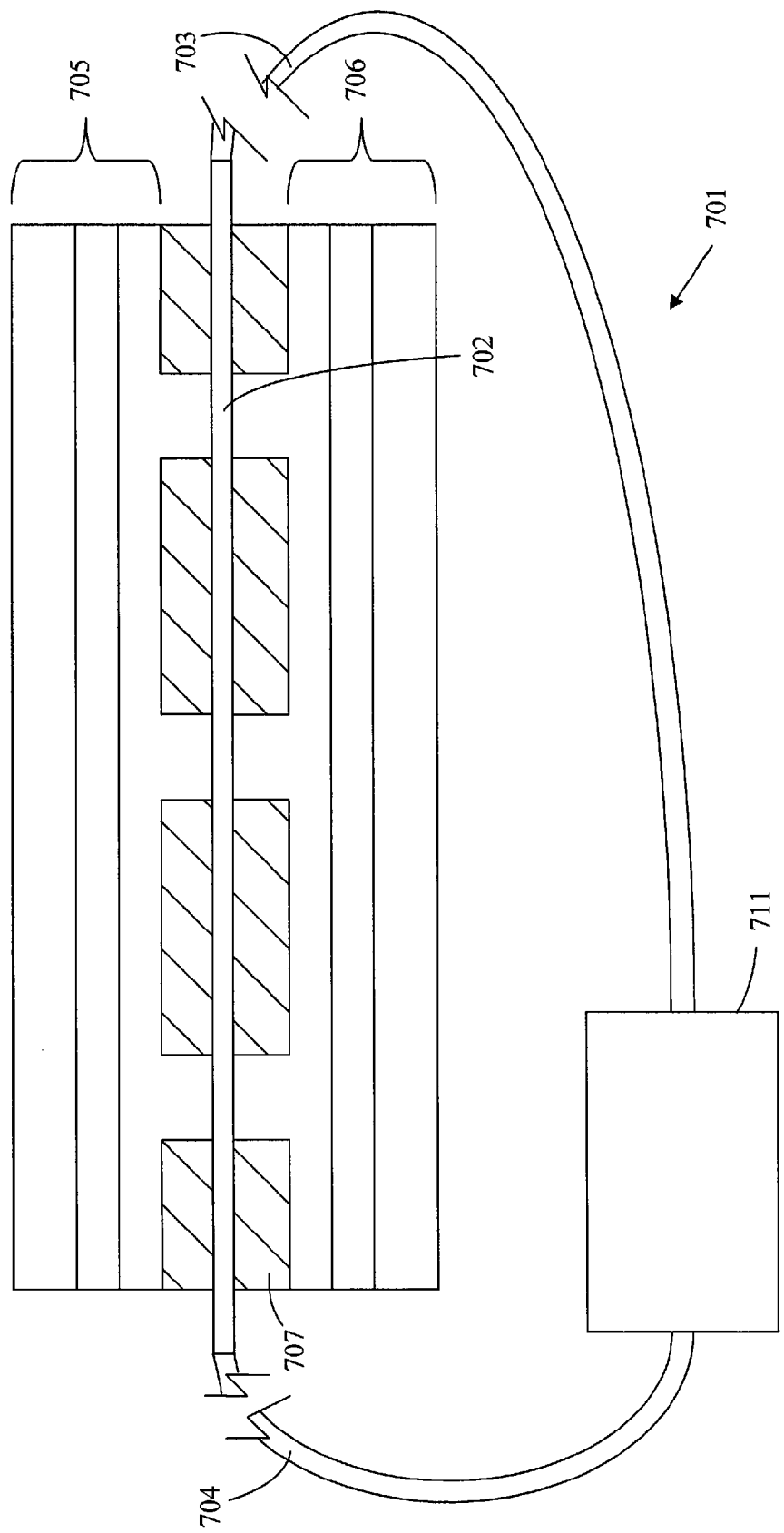
FIG. 7 illustrates generally an electric defibrillator according to the subject matter disclosed herein.

FIG. 7 illustrates generally one embodiment of defibrillator 701 adapted to thaw electrodes 705 and 706 according to the subject matter disclosed herein. Pre-connected electrodes 705 and 706 are similar to pre-connected electrodes 322 and 323 as illustrated in FIG. 3c, and further include electrode separator 707 similar to electrode separator 320. However, the embodiment illustrated in FIG. 7 further includes resistive heating element 702. Resistive heating element 702 is embedded in electrode separator 707. Resistive heating element 702 is adapted to include leads 704 and 703. Leads 703 and 704 are further adapted to be connected to the base 711 and power source of the defibrillator via conductors 713 and 715 such that a current may be driven through resistive heating element 702. Resistive heating element 702 is adapted to emit heat and thus thaw electrodes 705 and 706. It is to be understood that resistive heating element 702 may be arranged in any structure to maximize the ability of resistive heating element 702 to dissipate heat to defrost the electrodes 705 and 706. In one example, resistive heating element 702 may be a serpentine structure as illustrated in FIG. 6b.

Figure 8:
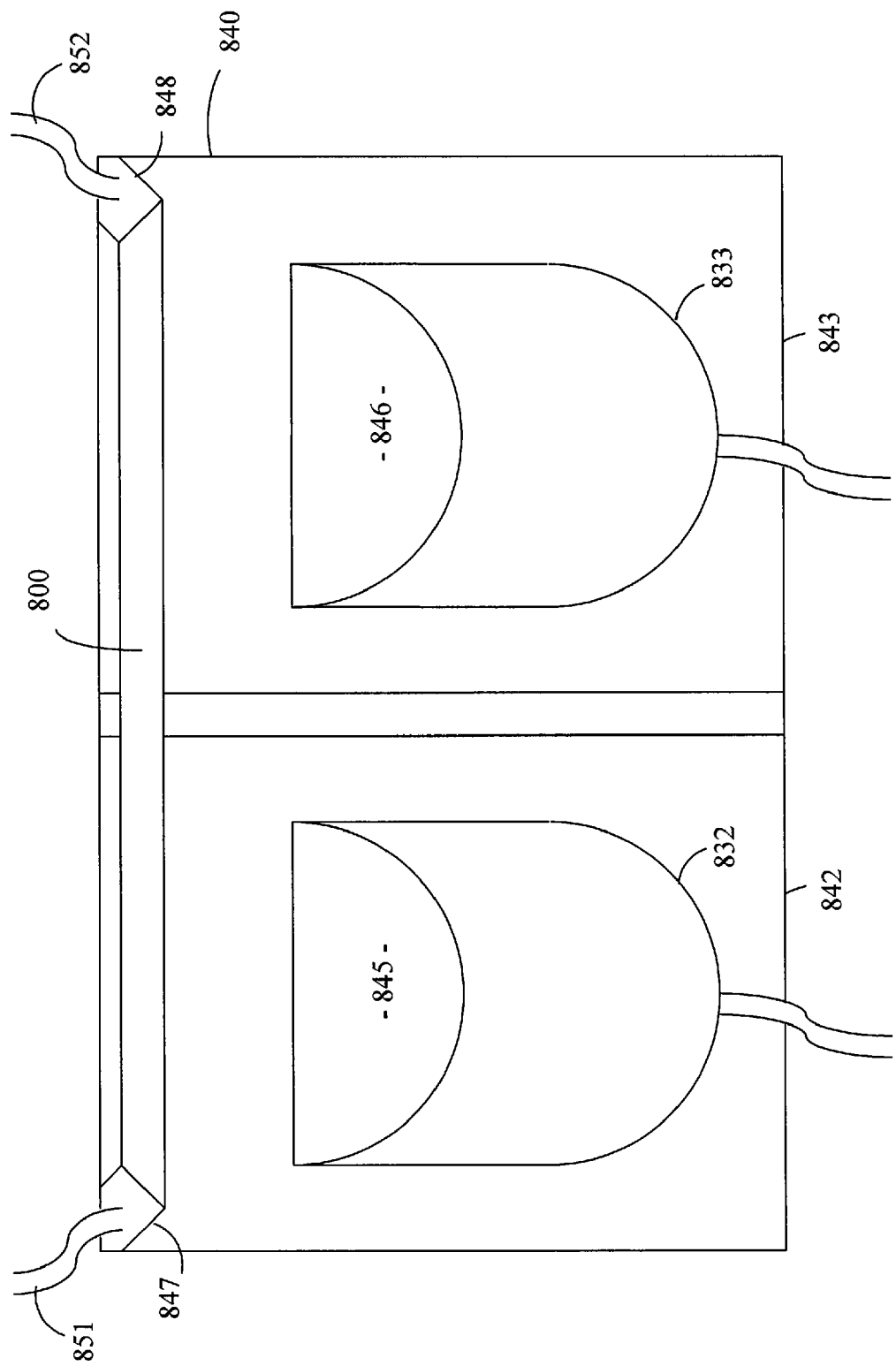
FIG. 8 illustrates generally an electric defibrillator according to the subject matter disclosed herein.

FIG. 8 illustrates generally one embodiment of defibrillator adapted to thaw electrodes 832 and 833 according to the subject matter disclosed herein. FIG. 8 includes a package 840 having two interior surfaces 842 and 843. Electrodes 832 and 833 and respective adhesive layers 845 and 846 are located on these interior surfaces and are partially folded back for illustration purposes. Package 840 is similar to package 340 of FIG. 3d, however, package 840 includes conductive element 800. Package 840 includes external connectors 847 and 848. Conductive element 800 provides an electrical connection between external connectors 847 and 848. According to this embodiment, conductive element 800 functions as a heating element. External connectors 847 and 848 are adapted to be connected to a power source through electrical connectors 851 and 852 and conductive element 800 such that heat is emitted into package 840. Package 840 acts as an insulator trapping emitted heat, and thus frozen electrodes 832 and 833 are thawed. It is to be understood that package 840 is used for illustration purposes only. Any package for electrodes may include conductive element 800 and external connectors 847 and 848 for purposes of thawing a frozen electrode. It is further to be understood that conductive element 800 may be arranged in any structure to maximize the ability of conductive element to dissipate heat into package 840. In one example, conductive element 800 may be a serpentine structure as illustrated in FIG. 6b.

Figure 9:
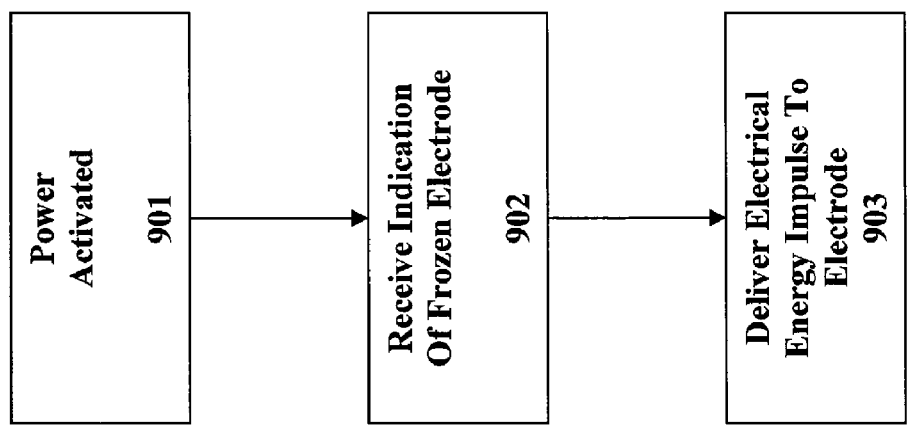
FIG. 9 illustrates generally a flow chart example of a method of defrosting an electrode according to the subject matter disclosed herein.

FIG. 9 illustrates one embodiment of a method of defrosting an electrode of an electric defibrillator according to the subject matter disclosed herein. According to the example of FIG. 9, a rescuer has access to an electric defibrillator 101, as shown generally in FIG. 1. Defibrillator 101 includes at least one frozen electrode 105. Electrode 105 may be frozen because, for example, it has been stored in an automobile in cold weather for a period of time. At 901, the power of defibrillator 101 is activated. At 902, controller 103 receives a signal initiated by rescuer that indicates electrode 105 is frozen. At 903, one or more pulses of electrical energy are delivered to electrode 105. In various embodiments, the delivery of electrical energy is at a level sufficient to defrost the electrode 105. In various embodiments, electrical energy is delivered such that damage to components of electrode 105 is minimized.

Figure 10:
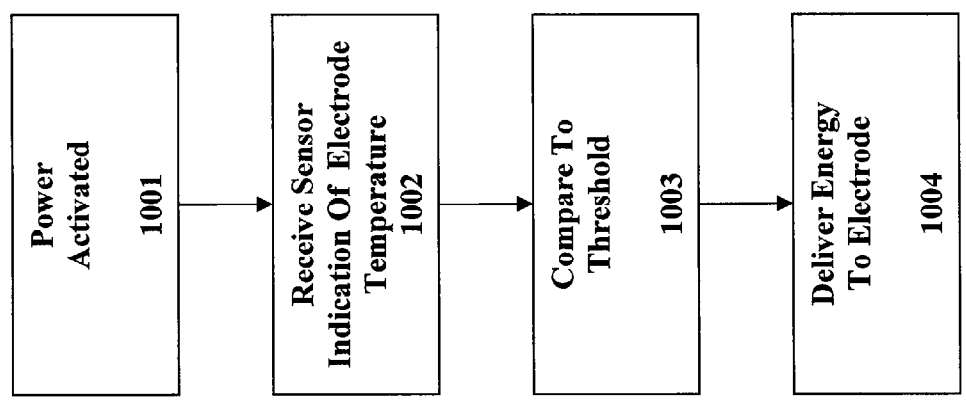
FIG. 10 illustrates generally a flow chart example of a method of defrosting an electrode according to the subject matter disclosed herein.

FIG. 10 illustrates one embodiment of a method of defrosting an electrode of an electric defibrillator 101 according to the subject matter disclosed herein. According to the example of FIG. 10 a rescuer has access to an electric defibrillator 101. Defibrillator 101 includes at least one frozen electrode 105. Defibrillator 101 further includes at least one sensor 108 adapted to measure a temperature of electrode 105 and communicate that temperature to controller 103. At 1001, the power of defibrillator 101 is activated. At 1002, controller 103 receives a signal from sensor 108 that indicates a measurement of temperature. At 1003, controller 103 is adapted to compare the temperature measurement to one or more thresholds. At 1004, if the measured temperature is below a particular threshold, controller initiates the delivery of one or more electrical impulses as discussed herein with respect to FIGS. 3a-e, 5, and 6. In various embodiments, controller 103 may be adapted to vary the duration or intensity of an electrical impulse based on the measured temperature of electrode 105, or any other condition internal or external to defibrillator 101. One or more pulses of electrical energy are delivered to electrode 105. In various embodiments, the delivery of electrical energy is at a level sufficient to defrost electrode 105. In various embodiments, electrical energy is delivered such that damage to components of electrode 105 is minimized.

Figure 11:
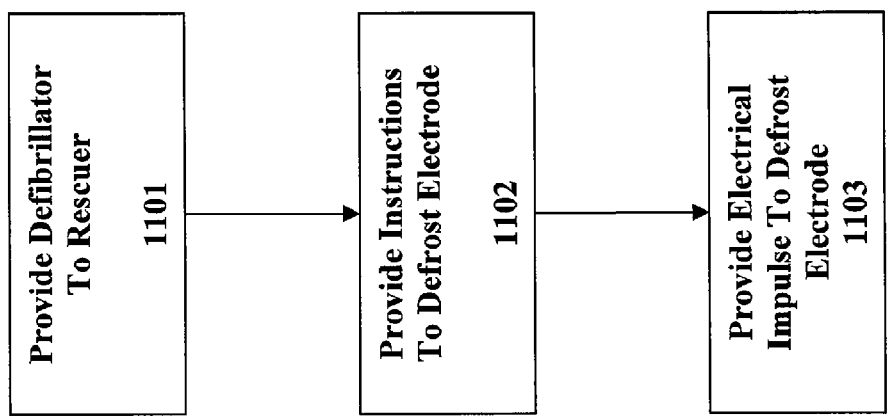
FIG. 11 illustrates generally a flow chart example of a method of assisting a rescuer to defrost an electrode according to the subject matter disclosed herein.

FIG. 11 illustrates generally one example of a method of assisting a rescuer to defrost electrode 105 of defibrillator 101. At 1101, electric defibrillator 101 is provided to a rescuer, Electrode 105 of defibrillator 101 is frozen. In one embodiment, sensors 108 of defibrillator 101 may determine that electrode 105 is frozen. In another embodiment, rescuer may determine that electrode 105 is frozen. At 1102, the rescuer is provided instructions to defrost electrode 105. In one embodiment, instructions may indicate to a rescuer how to initiate the defrosting of electrode 105. In other embodiments, instructions may indicate that controller 103 has initiated defrosting electrode 105. In yet other embodiments, controller 103 may initiate defrosting of electrode 105 automatically. At 1103, an electrical impulse is provided sufficient to defrost electrode 105 as discussed herein with respect to FIGS. 3a-e, 5, 6a-b, 7, and 8. In various embodiments, electrical energy is delivered such that damage to components of electrode 105 is minimized.

Figure 12:
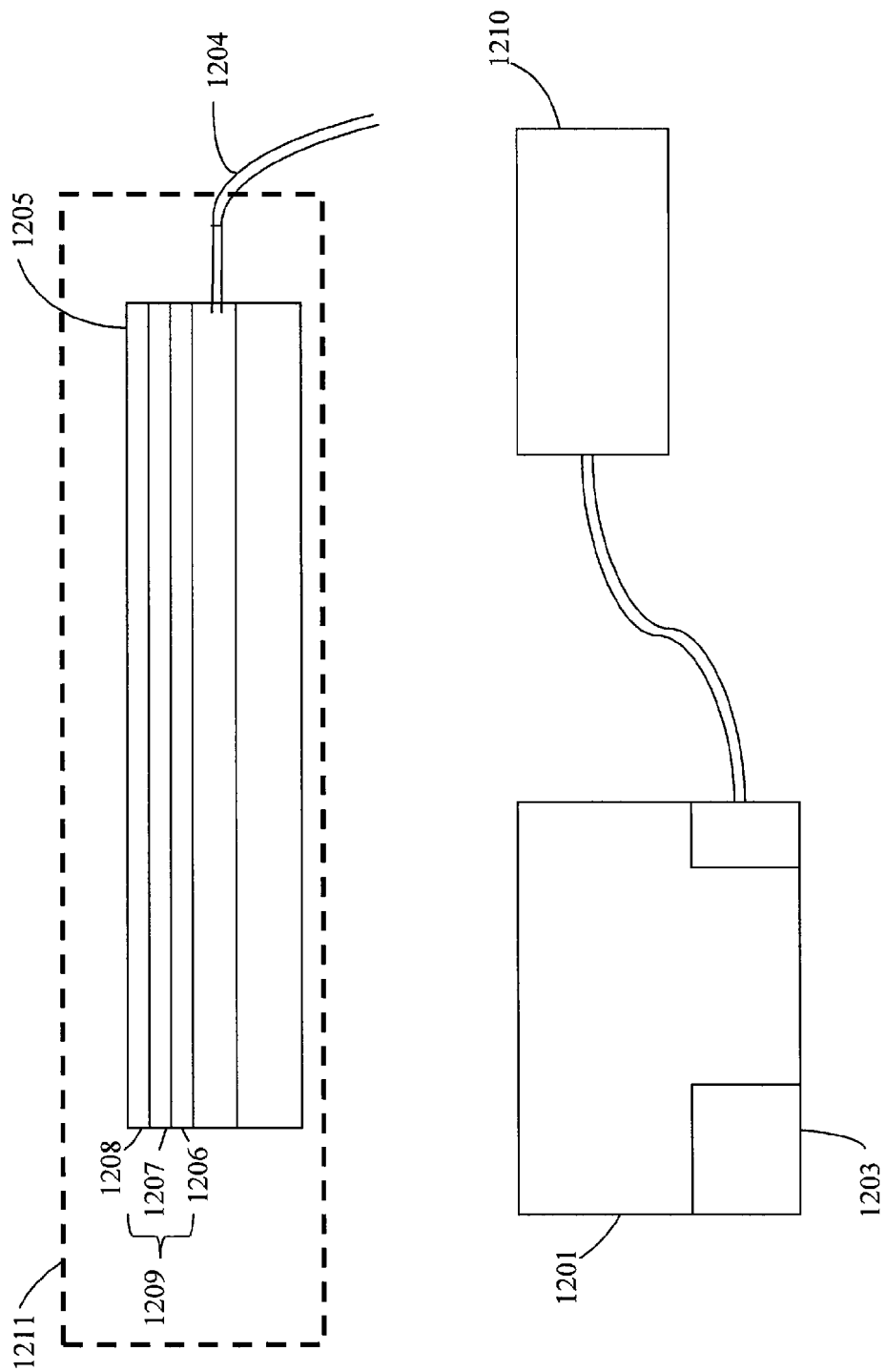
FIG. 12 illustrates generally an electric defibrillator according to the subject matter disclosed herein.

FIG. 12 illustrates generally an example of electric defibrillator 1201 according to the subject matter disclosed herein. Electric defibrillator 1201 includes electrode defroster 1210. In one embodiment, electrode defroster 1210 is coupled to electric defibrillator 1201. In another embodiment, electrode defroster 1210 is a component separate to defibrillator 1201. In an embodiment, controller 1203 is adapted to initiate, adjust, and/or monitor electrode defroster 1210. Defibrillator 1201 also includes electrode 1205. In various embodiments, electrode 1205 is stored in package 1211. In one embodiment, electrode defroster 1210 is adapted to be positioned proximally to package 1211 to defrost electrode 1205. In one embodiment, electrode defroster 1210 is adapted to be positioned proximally to electrode 1205 outside of package to defrost electrode 1205. In one embodiment, electrode defroster 1210 is adapted to contact electrode pouch 1211 to defrost electrode 1205. In one embodiment, electrode defroster 1210 is adapted to be positioned proximally to electrode 1205 outside of package to defrost electrode 1205. In various embodiments, electrode defroster 1210 is adapted to contact at least one portion of electrode 1205. In one embodiment, electrode defroster 1210 is adapted to contact lead 1204 of electrode 1205. In another embodiment, electrode defroster 1210 is adapted to contact conductive portion 1206 of electrode 1205. In yet another embodiment, electrode defroster is adapted to contact patient contact portion 1209 of electrode 1205.

In various embodiments, electrode defroster 1210 is adapted to deliver energy to electrode 1205. In various embodiments, electrode defroster 1210 is adapted to deliver energy in the form of electrical energy to electrode 1205. According to these embodiments, electrical energy is applied to one or more portions of electrode 1205 such that electrical energy is converted to heat. In one embodiment, electrical energy is applied to lead 1204 of electrode 1205. In another embodiment, electrical energy is applied to conductive layer 1206 of electrode 1205. In another embodiment, electrical energy is applied to hydrogel layer 1207 of electrode 1205. In another embodiment, electrical energy is applied to foil layer 1208. In various alternative embodiments, electrode defroster is adapted to deliver heat directly to electrode 1205. In one embodiment, electrode defroster is a heat element. In various embodiments, electrode defroster is placed proximally to any portion of electrode 1205 to defrost it.

Figure 13:
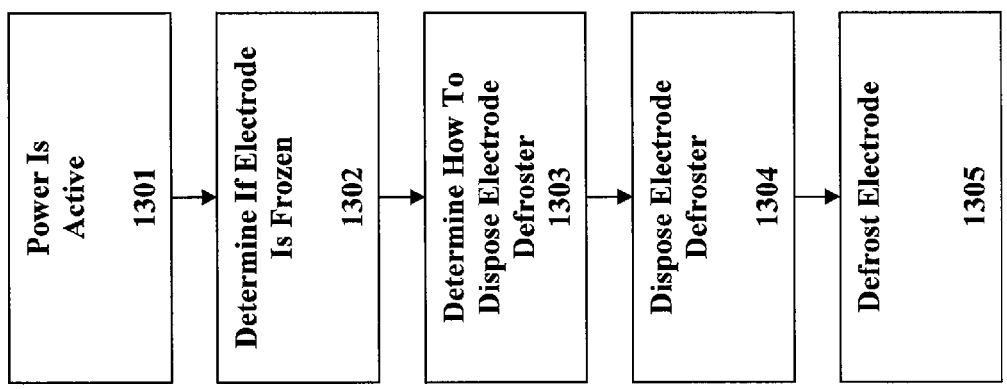
FIG. 13 illustrates generally a flow chart example of a method of assisting a rescuer to defrost an electrode according to the subject matter disclosed herein.

In one embodiment, electrode defroster 1210 is powered by defibrillator 1201. In another embodiment, electrode defroster is powered by a power source external to defibrillator 1201. FIG. 13 illustrates generally a flow chart example of a method defrosting an electrode according to the subject matter disclosed herein. FIG. 13 illustrates one embodiment of a method of defrosting an electrode of an electric defibrillator 1201 according to the subject matter disclosed herein. According to the example of FIG. 13, a rescuer has access to an electric defibrillator 1201. Defibrillator 1201 includes at least one frozen electrode 1205. Defibrillator 1201 further includes at least one electrode defroster 1210. At 1301, the power of defibrillator is active. At 1302, a rescuer determines that electrode 1205 is frozen. At 1303, rescuer determines how to dispose electrode defroster 1210 in relation to electrode 1205. At 1304, rescuer disposes electrode defroster 1210 proximally to or in contact with electrode 1205. At 1305, electrode defroster 1210 thaws electrode 1205.

Figure 14:
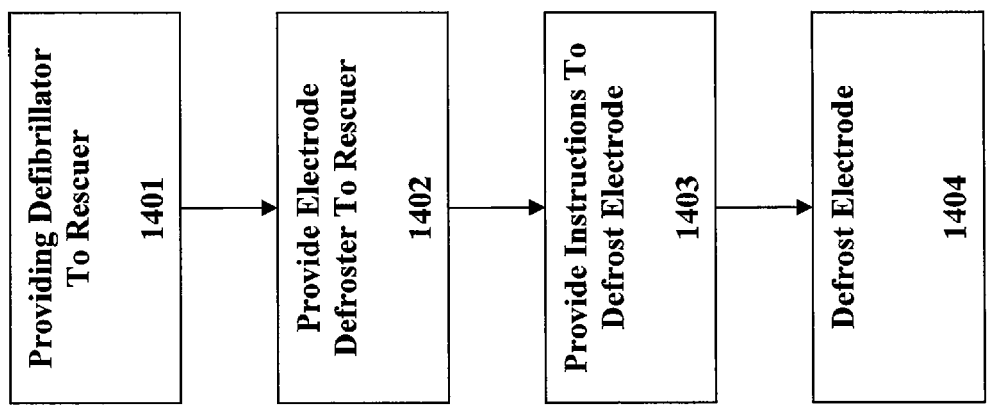
FIG. 14 illustrates generally a flow chart example of a method of assisting a rescuer to defrost an electrode according to the subject matter disclosed herein.

FIG. 14 illustrates generally a flow chart example of a method of assisting a rescuer to defrost electrode 1205. At 1401, defibrillator 1205 is provided to a rescuer. Electrode 1205 of defibrillator 1201 is frozen. At 1402, electrode defroster 1210 is provided to rescuer. At 1403, instructions to use electrode defroster 1210 to defrost electrode 1205 are provided to rescuer. At 1404 the rescuer positions electrode defroster 1210 as directed by instructions provided at 1403. At 1404 electrode defroster 1210 delivers energy to defrost electrode 1205.

Figure 15:
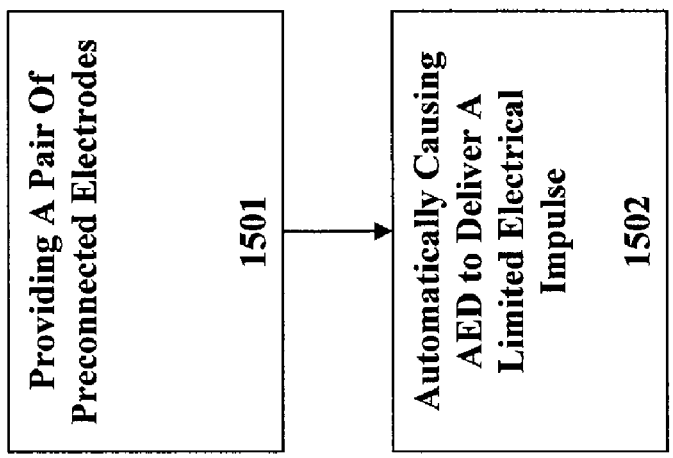
FIG. 15 illustrates generally a flow chart example of a method of controlling the operating conditions of a defibrillation electrode according to the subject matter disclosed herein.

FIG. 15 illustrates a similar embodiment of a method of controlling the operating conditions of defibrillation electrodes of an automated external defibrillator. First, at 1501 a pair of preconnected electrodes is provided which are adapted to releasably attach to an external portion of a patient. The electrodes generally attachable to the chest of a patient needing resuscitation. Each of the electrodes provided has a conductive interface medium having physical properties dependent upon a desired temperature range of about 32° F. to 122° F. At 1502, the AED is automatically caused to deliver a limited electrical impulse to the defibrillation electrodes so as to heat the defibrillation electrodes to the desired temperature range. Using a sensor to indicate if the electrode is frozen may be included in this method. Further, such a process may utilize a resistive heating element or be done during operation of the AED prior to delivery of a defibrillator pulse through the electrodes.

In each of the methods and apparatus for defrosting defibrillation electrodes discussed in this application, current shall be kept low enough to prevent damaging local heating effects. Such parameters depend on the construction of the individual specific electrode. The pulse duration and periodicity of the current shall be compatible with the specific electrode type and characteristics to allow for an even and non-destructive energy absorption by the electrodes to effect an even and successful defrosting. A preferred pulse energy may be about 10 to 20 Joules, for example. In some embodiments, the number of pulses may be determined by the initial temperature of the electrodes and the mass of the electrodes. Also, in some embodiments, the time between pulses may be determined by the ability of a specific electrode to absorb thermal energy. Generally, the voltage used shall be low enough to avoid internal arcing and to keep the current low enough to prevent excessive local heating. For example, a preferred embodiment could use a voltage range of 50 to 500 Volts.

Battery life of a defibrillator is generally only minimally affected by the use of the heating element as in most embodiments, the defrost is only utilized when needed and as needed. Total defrosting energy may be approximately in the 200 J range in some embodiments which may be roughly equivalent to one low energy defibrillation shock. Also, when using the foil layer as a resistive element, resistance is generally kept low enough not to interfere with the defibrillation function. This might be below 5 Ohms, in some embodiments, for example.

A variety of safety features are possible to avoid danger associated with energy impulses used to defrost electrodes as set forth. Typically, when the electrodes are contained in the packaging, there will be no hazard. Some devices may utilize features to detect if this packaging is torn. Safety can also be insured via voice and/or visual prompts similar to those used when energy is being delivered to the patient. When defrosting is in progress, the user will be instructed to not handle nor open the electrode pouch. When defrosting is complete, the normal prompting sequence can be resumed.

Safety will also be ensured as current will be limited by controlling the voltage on the caps since the impedance range for the electrode is predictable within a sufficient degree of certainty.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

Additional disclosure material that exemplifies at least a portion of the other features and functionality of the range of embodiments within the spirit and scope of the present invention can be found in U.S. Pat. Nos. 5,697,955, 5,817,151, 5,402,884, 5,579,919, 5,850,920, 5,984,102, 6,148,233 5,645,571, 5,792,190, 5,797,969, 5,919,212, 5,700,281, 6,029,085, 5,897,576, 6,173,203, 6,246,907, 6,263,238, 6,289,243, 7,006,865, 7,020,520, 6,658,290, 6,993,386, 6,321,113, 6,668,192, 7,065,401 5,955,956, and 5,897,576 the disclosures of which are hereby incorporated by reference in their entireties.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An automated external defibrillator with defrosting capabilities comprising:
   a portable housing containing a battery powered energy source and a controller; and
   at least a pair of electrodes operably coupled to the housing, the electrodes being releasably attachable to an external portion of a patient in need of resuscitation, each of the electrodes including a conductive interface medium having physical properties dependent upon a desired temperature range of about 32° F. to 122° F.;
   wherein the controller is configured to selectively heat the conductive interface medium by applying a limited amount of electrical impulse from the energy source to raise the temperature of the conductive interface medium toward the desired range.

2. The defibrillator of claim 1, wherein the conductive interface medium is hydrogel.

3. The defibrillator of claim 1, wherein the conductive interface medium is an adhesive composition.

4. The defibrillator of claim 1, wherein the conductive interface medium is a nanopillar tape.

5. The defibrillator of claim 1, further comprising a temperature sensor operably connected to the controller, wherein the controller heats the conductive interface medium in response to data from the temperature sensor.

6. The defibrillator of claim 1, further comprising a motion sensor operably coupled to the controller wherein the controller heats the conductive interface medium in response to a signal from the motion sensor indicative of movement or opening of the defibrillator.

7. The defibrillator of claim 1, wherein the electrodes further include a resistive element that is heated by impulses from the energy source to heat the conductive interface medium.

8. The defibrillator of claim 7, wherein the resistive element has a serpentine configuration.

9. The defibrillator of claim 7, wherein the resistive element is located between a pair of preconnected electrodes.

10. The defibrillator of claim 7, further including an electrode package adapted to contain the resistive element and house the electrodes.

11. An automated external defibrillator with defrosting capabilities comprising:
a pair of preconnected electrodes including an outer hydrogel layer on each electrode having physical properties dependent upon a normal temperature range of about 32° F. to 122° F.; and
a housing including a battery powered energy source and a controller that selectively heats the hydrogel layer by applying a limited amount of electrical impulse to raise the temperature of the hydrogel layer to the normal range.

12. The defibrillator of claim 11, further comprising a temperature sensor having temperature sensor outputs, said temperature sensor operably coupled to the controller, wherein the controller applies the limited electrical impulses in response to said temperature sensor outputs.

13. The defibrillator of claim 11, further comprising a motion sensor for sensing defibrillator movement, said motion sensor operably coupled to the controller, wherein the controller applies the limited electrical impulses in response to said defibrillator movement.

14. The defibrillator of claim 11, further including a package in which the preconnected electrodes are stored in a package containing a heating element.

15. The defibrillator of claim 11, further including a resistive heating element.

16. A method of controlling the operating conditions of defibrillation electrodes of an automated external defibrillator, comprising:
providing a pair of electrodes releasably attachable with an external portion of a patient in need of resuscitation, each electrode having a conductive interface medium having physical properties dependent upon a desired temperature range of about 32° F. to 122° F.; and
automatically causing the automated external defibrillator to deliver a limited electrical impulse to the defibrillation electrodes so as to heat the defibrillation electrodes to the desired temperature range.

17. The method of claim 16, further including the step of providing a sensor to indicate when the defibrillation electrode is frozen and performing the step of automatically causing the automated external defibrillator to deliver a limited electrical impulse to the defibrillation electrodes in response to the sensor.

18. The method of claim 16, wherein the step of automatically causing the automated external defibrillator to deliver a limited electrical impulse to the defibrillation electrodes causes the limited electrical impulse to be conducted through a resistive heating element to thaw the electrode.

19. The method of claim 16, wherein the steps are done during operation of the automated external defibrillator prior to delivery of a defibrillation pulse through the defibrillation electrodes.

* * * * *

UNITED STATES PATENT AND TRADEMARK OFFICE
CERTIFICATE OF CORRECTION

PATENT NO. : 7,881,785 B2
APPLICATION NO. : 12/055817
DATED : February 1, 2011
INVENTOR(S) : Rabih C. Nassif et al.

It is certified that error appears in the above-identified patent and that said Letters Patent is hereby corrected as shown below:

On the Title Page of the patent please correct as follows:

(75) Inventors: Rabih C. Nassif, Delete "Bothell, WA" and insert --Corona, CA--
Peter M. Peterson, Delete "Bothell, WA" and insert --Mission Viejo, CA--

Signed and Sealed this
Twenty-seventh Day of September, 2011

David J. Kappos
*Director of the United States Patent and Trademark Office*